United States Patent
Youssef

(10) Patent No.: US 8,080,030 B2
(45) Date of Patent: Dec. 20, 2011

(54) ENDOSCOPIC SHEATH HAVING A BIOMIMETIC RETRACTOR

(75) Inventor: Ashraf Samy Youssef, Tampa, FL (US)

(73) Assignee: University of South Florida, Tampa, FL (US)

( * ) Notice: Subject to any disclaimer, the term of this patent is extended or adjusted under 35 U.S.C. 154(b) by 840 days.

(21) Appl. No.: 11/307,088

(22) Filed: Jan. 23, 2006

(65) Prior Publication Data

US 2006/0200003 A1 Sep. 7, 2006

Related U.S. Application Data

(60) Provisional application No. 60/645,923, filed on Jan. 21, 2005.

(51) Int. Cl.
*A61M 29/00* (2006.01)

(52) U.S. Cl. ..................................... 606/192

(58) Field of Classification Search .............. 604/22, 604/26, 264, 278, 35, 164.11, 164.03, 165.02, 604/158, 164.01, 167.01, 167.02, 96.01; 606/205, 207, 1, 46, 232, 148, 144, 138, 606/158, 213, 180, 185, 171, 167, 114, 190, 606/191, 192, 108; 600/184, 116, 121, 138, 600/201, 203, 204
See application file for complete search history.

(56) References Cited

U.S. PATENT DOCUMENTS

| | | | | |
|---|---|---|---|---|
| 4,141,364 A * | 2/1979 | Schultze | ................. | 128/207.15 |
| 4,312,353 A * | 1/1982 | Shahbabian | ................. | 606/192 |
| 4,338,942 A * | 7/1982 | Fogarty | ................. | 606/194 |
| 4,676,228 A * | 6/1987 | Krasner et al. | ................. | 600/116 |
| 5,178,608 A * | 1/1993 | Winters | ................. | 604/102.02 |
| 5,213,576 A * | 5/1993 | Abiuso et al. | ................. | 604/103.01 |
| 5,290,306 A * | 3/1994 | Trotta et al. | ................. | 606/194 |
| 5,330,446 A * | 7/1994 | Weldon et al. | ................. | 604/271 |
| 5,391,178 A * | 2/1995 | Yapor | ................. | 606/192 |
| 5,505,210 A * | 4/1996 | Clement | ................. | 600/566 |
| 5,702,417 A * | 12/1997 | Hermann | ................. | 606/194 |
| 5,833,658 A * | 11/1998 | Levy et al. | ................. | 604/97.01 |
| 5,865,802 A * | 2/1999 | Yoon et al. | ................. | 604/104 |
| 5,951,513 A * | 9/1999 | Miraki | ................. | 604/96.01 |
| 5,967,970 A * | 10/1999 | Cowan et al. | ................. | 600/207 |
| 6,171,299 B1 * | 1/2001 | Bonutti | ................. | 606/1 |
| 6,306,162 B1 * | 10/2001 | Patel | ................. | 623/1.11 |
| 6,692,494 B1 * | 2/2004 | Cooper et al. | ................. | 606/46 |
| 6,695,858 B1 * | 2/2004 | Dubrul et al. | ................. | 606/159 |
| 2001/0018596 A1 * | 8/2001 | Selmon et al. | ................. | 606/198 |
| 2001/0047147 A1 * | 11/2001 | Slepian et al. | ................. | 604/22 |
| 2002/0007146 A1 * | 1/2002 | Omaleki et al. | ................. | 604/103.09 |
| 2002/0095114 A1 * | 7/2002 | Palasis | ................. | 604/96.01 |
| 2003/0225432 A1 * | 12/2003 | Baptiste et al. | ................. | 606/191 |
| 2004/0002680 A1 * | 1/2004 | Ackerman et al. | ................. | 604/96.01 |
| 2004/0073162 A1 * | 4/2004 | Bleam et al. | ................. | 604/103 |
| 2004/0098015 A1 * | 5/2004 | Weikel et al. | ................. | 606/192 |
| 2004/0102681 A1 * | 5/2004 | Gross | ................. | 600/116 |
| 2004/0230218 A1 * | 11/2004 | Criscuolo et al. | ................. | 606/190 |
| 2004/0236366 A1 * | 11/2004 | Kennedy et al. | ................. | 606/192 |

* cited by examiner

*Primary Examiner* — Ryan Severson
*Assistant Examiner* — David Eastwood
(74) *Attorney, Agent, or Firm* — Ronald E. Smith; Smith & Hopen, P.A.

(57) ABSTRACT

An endoscopic sheath having a biomimetic retractor for retracting organs and tissues in the body. The inflatable retractor comprises an inflatable balloon configured to retract specific organs and tissues at the site of the endoscopic procedure, with attached inflation and deflation means. In one embodiment, the inflatable retractor is attached to an outer tube or cannula. A second, inner cannula is placed within the outer cannula and attached thereto by a plurality of substantially elastic strands. The strands center the inner cannula while allowing it to be manipulated in any direction.

3 Claims, 5 Drawing Sheets

ENDOSCOPIC SHEATH HAVING A BIOMIMETIC RETRACTOR

CROSS REFERENCE TO RELATED APPLICATIONS

This application claims benefit of pending provisional U.S. Ser. No. 60/645,923 filed Jan. 21, 2005.

BACKGROUND OF THE INVENTION

1. Field of the Invention

The present invention relates to retractors used in surgery, and more specifically, to an inflatable retractor by which an internal organ or other internal body part may be retracted during endoscopic surgery.

2. Background of the Invention

The field of endoscopic surgery has been advancing rapidly in recent years. In this form of surgery, procedures are performed inside the body of a patient using instruments inserted through small incisions or ports in the body. The surgery is performed with the aid of an endoscope, which is a thin, tube-like instrument featuring a light source, viewing lenses, and/or various other attachments such as irrigators, scissors, snares, brushes or forceps. Endoscopes may be flexible or rigid, and normally utilize optic fibers to transmit light to the internal cavity. This form of surgery allows internal visualization of the body structure without the necessity of excessive dissection of tissue. Typical endoscopes are in the 5 to 12 mm diameter range and thus require only very small incisions for insertion into the body.

Endoscopic surgery has developed rapidly because of the numerous benefits arising in favor of the patient. Since there is only a small incision to permit the entrance of the endoscope and other endosurgical devices, endoscopic surgery results in less trauma to the patient's body and faster patient recovery. For the benefits of endoscopic surgery to arise, however, all aspects of the surgery, such as the initial examination, retraction of internal organs, and the surgical procedure itself, must be capable of being performed through small endoscopic incisions or ports.

Endoscopic surgery has particular utility in the field of neurosurgery where, for obvious reasons, it is especially desirable to disrupt and/or manipulate as little tissue as possible. Certain tumors, such as those of the Pineal Gland, benefit from such procedures as direct surgery can be curative for benign tumors as well as providing a generous sample for biopsies leading to a definite diagnosis. Direct surgery using traditional stereotactic or endoscopic techniques can result in complications, including EOM dysfunction, altered mental status, hemorrhage, extrapyramidal symptoms, hemiparesis, hemianopsia and seizures. Traditional endoscopic procedures are further complicated due to the use of flexible endoscopes which can be technically difficult to maneuver.

Therefore, what is needed is a minimally invasive device that would allow surgery to be safely performed on microsurgical anatomy of neurological structures, such as the pineal region of the brain. The ideal device would provide for frameless stereotactic guidance and use a rigid neuroendoscope

SUMMARY OF INVENTION

The present invention provides an apparatus and method for improved endoscopic retraction procedures. The invention permits safe and effective retraction of internal organs and tissue thereby providing protection to delicate structures during an endoscopic procedure.

Retraction is accomplished with the present invention through the use of an inflatable bladder or membrane attached to an endoscopic sheathe. The membrane is sufficiently soft and flexible enough to avoid damage to internal organs and tissues, yet it is sufficiently inelastic and rigid so as to provide retraction when inflated.

In accordance with one aspect of the present invention, there is provided an inflatable endoscopic retractor comprised of an inflatable membrane having an anatomical configuration designed to retract structures specific to the surgical procedure. For example, the membrane for use in an endoscopic biopsy would be configured to retract the cerebrum and cerebellum, as well as to provide protection thereto. The present invention is not limited to neurosurgical applications. Analogous anatomical membranes for use in other procedures include configurations for other anatomical structures; e.g. the kidney, bladder, pancreas and liver.

When retraction during endoscopic surgery is desired, the endoscopic sheath is inserted into the body. The distal end of the inner tube is placed, under direct view, proximal to the anatomical structure that is the subject of the procedure. The membrane may be slightly inflated to assist in its proper positioning inside the body. Once the distal end of the inner cannula is properly positioned, the membrane is inflated with air or other gas or liquid, in an amount sufficient to retract the desired organ or other tissue and maintain and support the organ or tissue in its retracted position. After the endoscopic procedure is complete, the membrane is deflated and the endoscopic sheath is removed.

In accordance with a second aspect of the present invention, there is provided an endoscopic sheath comprising a substantially rigid elongate outer cannula or tube, and a substantially rigid, elongated inner cannula or tube. The inner cannula is of sufficient diameter to pass through the lumen of the outer cannula and may be manipulated along any axis therein. At least one, but preferably more, flexible suspension strand extends radially between the inner and outer cannula and connects the outer surface of the inner cannula to the inner surface of the outer cannula. The at least one suspension strand is substantially elastic in a radial direction as depicted to provide maximum mobility for the inner cannula within the lumen of the outer cannula. The at least one flexible suspension strand is radially positioned to connect the inner and outer cannulas such that the inner cannula assumes a position of repose where its longitudinal axis of symmetry is coincident with the longitudinal axis of symmetry of the outer cannula. An inflatable membrane is disposed in encircling relation to the elongate outer tube.

In accordance with another aspect of the present invention, there is provided a method of retracting internal tissue and organs using the retractor and sheathe described above. The inflatable membrane of the endoscopic sheath of the present invention significantly reduces the risks associated with retraction, such as thermal, electrical, or mechanical injury. In addition, it significantly reduces the chances of hemorrhage associated with direct surgery of neural tissue. The endoscopic sheathe is sufficiently small to allow its introduction into utilizing a small trocar. The sheath is normally introduced through a single small opening or burr hole.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
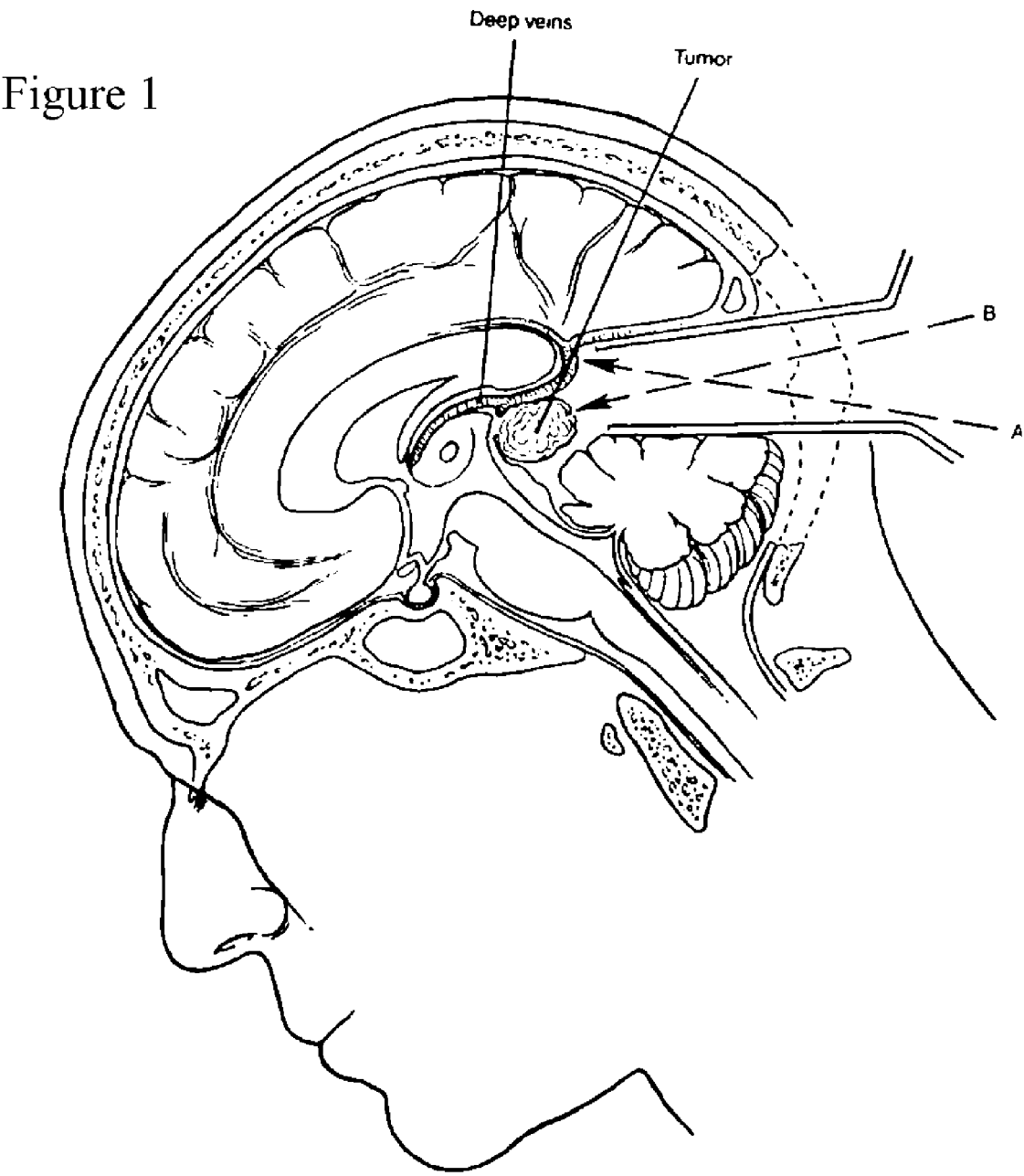
FIG. 1 is a sagittal view of a patient with a pineal region tumor.

Referring to FIG. 1, there is shown a sagital view of a patient undergoing an endoscopic biopsy of the pineal gland, illustrating only one example in which the endsoscopic sheath and retractor 5 of the present invention might be utilized during endoscopic surgery. In the example shown, a extra-ventricular trajectory is taken. Endosurgical port A is shown, through which endoscopic sheath 5 is inserted. This allows the surgeon to view the internal tissues and organs in the surgical area.

Sheath 5 of the present invention is inserted through the opening or port A made in the patient's body. A pair of endosurgical forceps may be inserted through surgical port A to aid in the positioning of the endoscopic sheath 5.

Figure 2:
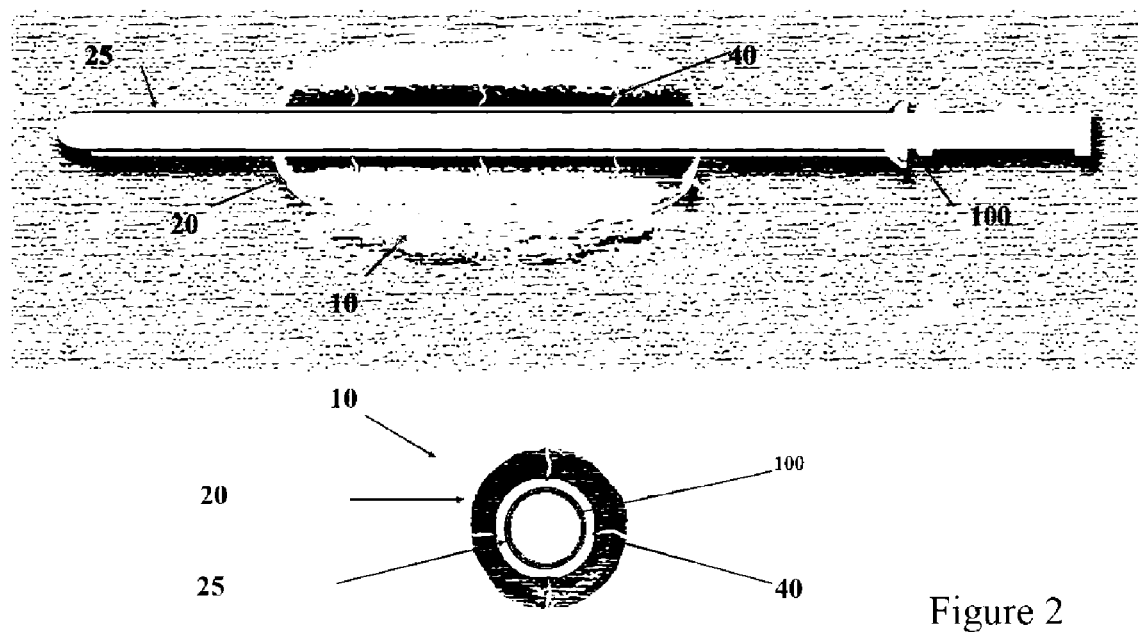
FIG. 2 provides perspective views of the inventive apparatus.
Figure 3:
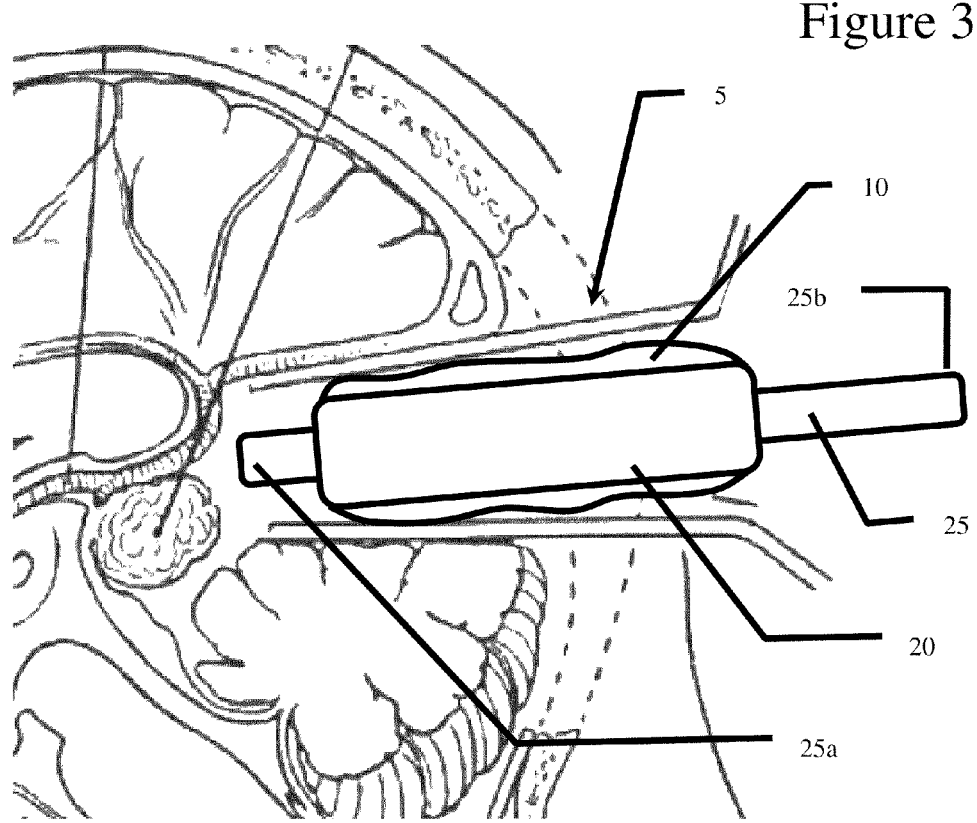
FIG. 3 is a sagittal view of a patient undergoing an endoscopic procedure wherein the inventive apparatus is introduced to the patient's body.

As illustrated in FIGS. 1-3, the inflatable retractor 10 of sheath 5 is used to constrain and retract the cerebrum and cerebellum to permit endosurgical access to the pineal region. It should be noted, however, that the principles of the present invention are not limited to any particular surgical procedure but may be applied to a wide variety of procedures and applications, including direct surgery.

Figure 4A:
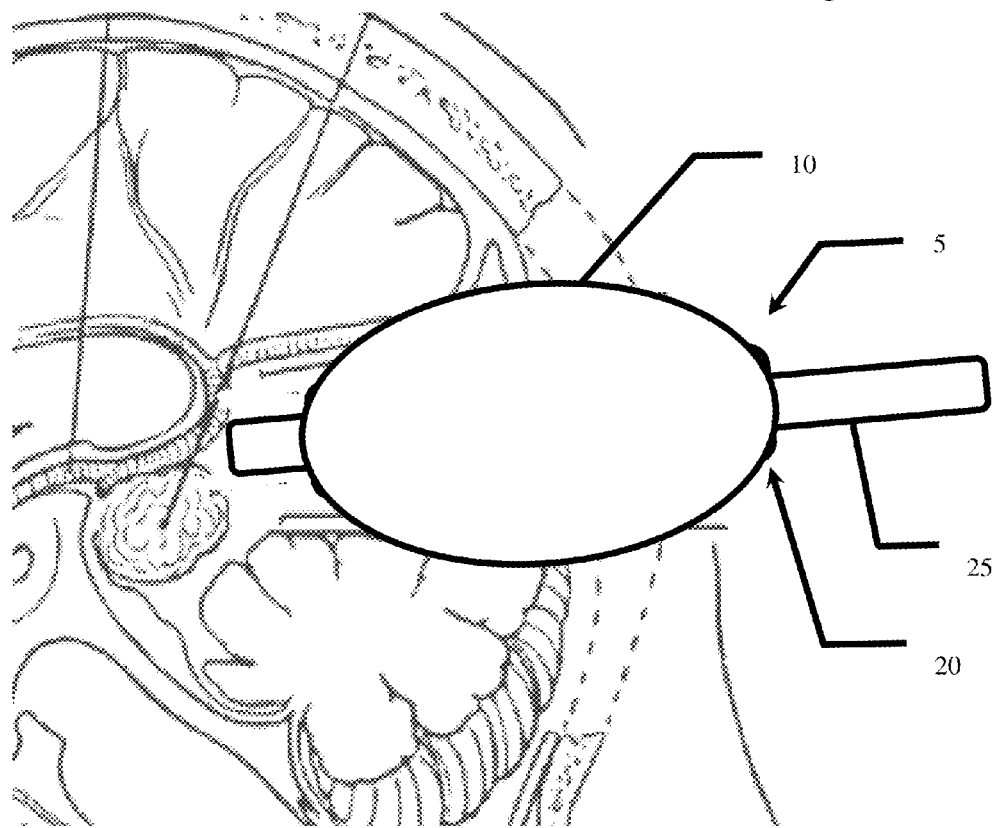
FIG. 4A is a sagittal view of a patient undergoing an endoscopic procedure wherein the membrane of the retractor is inflated.
Figure 4B:
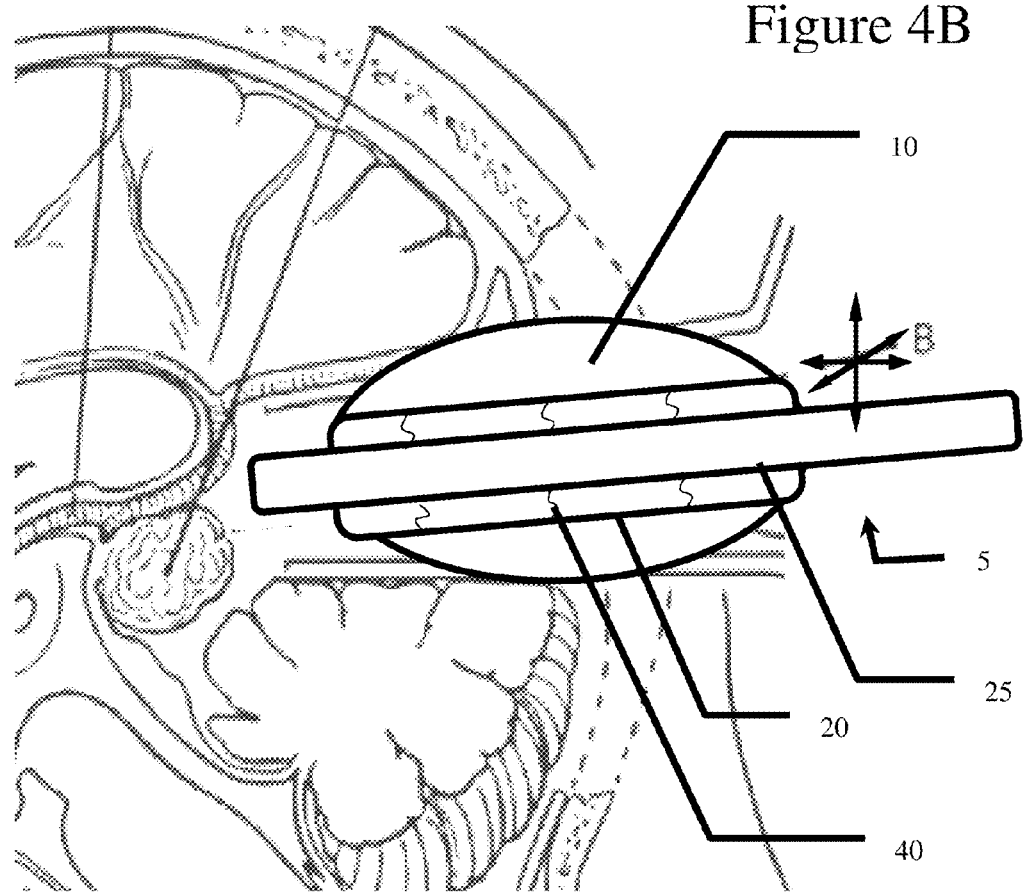
FIG. 4B is a sagittal view of a patient undergoing an endoscopic procedure wherein the membrane of the retractor is inflated the inventive apparatus is shown in cross-section and the suspension strands can be seen.

Referring now to FIGS. 2-4, there is shown one embodiment of endoscopic sheath 5 with inflatable retractor 10 of the present invention. FIG. 2 illustrates retractor 10 mounted on outer cannula 20 suitable for use in endoscopic procedures. The length of outer cannula 20 is primarily dependent upon the type of procedure in which the retractor is to be used.

Inner cannula 25 has a proximal or control end 25b, and a distal or insertion end 25a. Both outer cannula 20 and inner cannula 25 are preferably made of a material which will remain free from degradation, are easily sterilized, and are biocompatible. The shape of the distal or insertion end 25a is chosen to aid in preventing the puncture or other injury to internal organs and tissue when sheath 5 is being manipulated inside the patient's body. Proximal end 25b remains outside the patient's body during the procedure.

Suspension strands 40 connect inner cannula 25 to outer cannula 20, thereby allowing the movement of inner cannula 25 in three axis once outer cannula 20 is secured. Suspension strands 40 are preferably adapted to return inner cannula 25 to a home position, substantially parallel to outer cannula 20, when no force is applied to inner cannula 25. This arrangement allows inner cannula 25 to be freely moveable thereby enabling manipulation of the endoscopic device away from delicate structures.

In addition to the cannula-housing shown in FIGS. 2-4, the present invention is also compatible with standard trocar-induced cannulas frequently utilized in endoscopic surgery. As such, the cannulas provide a port into the patient's body and a short tube for the insertion of endoscopic instruments. Thus, the principles of the present invention are not to be limited to any particular housing, cannula, or method of insertion into the patient's body.

Still referring to FIG. 2, the inflatable retractor 10 consists of a long, inflatable balloon or membrane with an anatomical configuration designed to retract structures specific to the surgical procedure. The membrane of retractor 10 is comprised of a soft, flexible material which preferably does not absorb liquid and is easily sterilized, such as silastic, rubber, vinyl, polyethylene, or other polymeric material.

A small-diameter hollow tube made of non-collapsible, flexible material which is connected to the membrane of retractor 10 at its proximal end. This hollow tube permits the entry and exit of gas or liquid to and from the inflatable membrane. The proximal end of the tube connects to an inflation and venting device (not shown). This device can be any of a variety of devices, including, for example, a bulb-type or piston-type syringe, a gas cartridge, or a fluid pump.

Operation Of The Sheath

The operation of the inflatable endoscopic retractor as used in a biopsy of a pineal-region tumor will now be explained, as illustrated in FIGS. 2 through 4. The body is first prepared by creating a burr-hole within the skull of the patient. Endoscopic sheath 5 is inserted into the patient's body through the burr-hole in the selected trajectory. The trajectory may be a natural anatomical compartment, for example: CSF cisterns in closed procedures, or through brain tissue in open transventricular procedures.

In this example, trocar 100 is positioned within inner cannula 25 prior to insertion. An endoscope (not shown) may also be inserted into the body to aid in visualizing the internal structures and to ensure the proper positioning. For example, a pair of forceps suitable for use in endoscopic surgery may be inserted to aid in the positioning of the sheath 5. Trocar 100 is removed leaving inner cannula 25 free for insertion of an endoscope, for example. Distal end 25a of inner cannula 25 can be placed in optimum position under vision by the endoscope.

In this example, trocar 100 is positioned within inner cannula 25 prior to insertion. An endoscope (not shown) may also be inserted into the body to aid in visualizing the internal structures and to ensure the proper positioning. A pair of forceps 70 suitable for use in endoscopic surgery may be inserted to aid in the positioning of the sheath 5. Trocar 100 is removed leaving inner cannula 25 free for insertion of an endoscope, for example. Distal end 25a of inner cannula 20 can be placed in optimum position under vision by the endoscope.

As illustrated in FIG. 3, retractor 10 is mounted to outer cannula 20 and positioned, under direct view or with the help of an endoscope, within the patient's body. The membrane of retractor 10 may be slightly inflated to aid in its maneuvering. Retractor 10 can now be inflated against the surrounding neurovascular structure to reposition them away from endoscopic manipulations. With retractor 10 inflated and distal end 25a of inner cannula 25 positioned near the structure of interest, here the pineal region tumor, the endoscopic procedure can be performed while protecting the surrounding neurovascular structures.

Retractor 10 is deflated, and the endoscope and sheath 5 are safely removed when the procedure is completed. Furthermore, the endoscopic sheath of the present invention provides for inspection of the working trajectory as the endoscopic devices are removed.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An endoscopic sheath, comprising:
   an elongate outer tube having a rigid structure;
   an elongate inner tube, having a rigid structure, concentrically disposed within a lumen of said elongate outer tube;
   an inflatable membrane disposed in encircling relation to said elongate outer tube so that said elongate outer tube is substantially held against movement when inserted into a patient's tissue and said inflatable membrane is inflated;
   a plurality of elongate elastic, flexible suspension strands disposed in interconnecting relation between the elongate inner tube and the elongate outer tube, said elongate elastic, flexible suspension strands extending radially outwardly with respect to said elongate inner tube and said elongate flexible suspension strands being elastic in said radial direction;
   said plurality of elongate elastic, flexible suspension strands defining three sets of longitudinally spaced elongate elastic, flexible suspension strands, each set of longitudinally spaced elongate elastic, flexible suspension strands comprising a plurality of said elongate elastic, flexible suspension strands disposed in equidistantly and circumferentially spaced apart relation to one another;
   said elongate inner tube has a longitudinal axis of symmetry coincident with a longitudinal axis of symmetry of said elongate outer tube when each of said elongate elastic, flexible suspension strands and said elongate inner tube is in a position of repose;
   said elongate inner tube having a lumen adapted to slidingly receive a surgical tool therewithin; and
   said elongate inner tube remaining within said lumen of said elongate outer tube when said inflatable membrane is inflated.

2. The endoscopic sheath of claim 1, further comprising:
   said inflatable membrane being constructed of a material selected from the group of materials consisting of silastic, rubber, vinyl, and polyethylene.

3. A method of using an endoscopic sheath, comprising the steps of:
   providing an elongate outer tube having a rigid structure;
   providing an elongate inner tube, having a rigid structure, and disposing said elongate inner tube within a lumen of said elongate outer tube in concentric relation thereto;
   disposing an inflatable membrane in encircling relation to said elongate outer tube;
   inflating said inflatable membrane so that said elongate outer tube is substantially held against movement when inserted into a patient's tissue and said inflatable membrane is inflated;
   disposing a plurality of elongate elastic, flexible suspension strands in interconnecting relation between the elongate inner tube and the elongate outer tube, said elongate elastic, flexible suspension strands extending radially outwardly with respect to said elongate inner tube and said elongate, elastic flexible suspension strands being elastic in said radial direction;
   spacing three sets of said plurality of elongate elastic, flexible suspension strands longitudinally along said elongate inner tube and elongate outer tube, each set of said elongate elastic, flexible suspension strands comprising a plurality of elongate elastic, flexible suspension strands in equidistantly and circumferentially spaced apart relation to one another;
   positioning each of said elongate elastic, flexible suspension strands so that said elongate inner tube has a longitudinal axis of symmetry coincident with a longitudinal axis of symmetry of said elongate outer tube when each of said elongate, flexible suspension strands and said elongate inner tube is in a position of repose;
   adapting said elongate inner tube to slidingly receive a surgical tool within a lumen of said elongate inner tube; and
   said elongate elastic, flexible suspension strands maintaining said elongate inner tube within said lumen of said elongate outer tube when said inflatable membrane is inflated;
   whereby said elongate outer tube and said elongate inner tube remain within the patient during a surgical procedure.

* * * * *